(12) United States Patent
Hsiao et al.

(10) Patent No.: US 10,490,430 B2
(45) Date of Patent: Nov. 26, 2019

(54) FLEXIBLE LINEAR SENSOR

(71) Applicant: Taiwan Semiconductor Manufacturing Co., Ltd., Hsin-Chu (TW)

(72) Inventors: Min-Chuan Hsiao, Hsin-Chu (TW); Meng-Tsung Lin, Hsin-Chu (TW); Chen-Wei Chen, Hsin-Chu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 15/797,969

(22) Filed: Oct. 30, 2017

(65) Prior Publication Data
US 2019/0131151 A1    May 2, 2019

(51) Int. Cl.
*H01L 21/67* (2006.01)
*G08B 21/18* (2006.01)
*G01N 27/04* (2006.01)
*G01N 27/12* (2006.01)

(52) U.S. Cl.
CPC ...... *H01L 21/67253* (2013.01); *G08B 21/182* (2013.01); *G01N 27/048* (2013.01); *G01N 27/121* (2013.01)

(58) Field of Classification Search
CPC .................. H01L 21/67253; G08B 21/182
USPC ........................................................ 73/29.05
See application file for complete search history.

(56) References Cited

U.S. PATENT DOCUMENTS

| | | | | |
|---|---|---|---|---|
| 4,206,632 A * | 6/1980 | Suzuki | ........... | G01M 3/165 174/11 R |
| 5,146,785 A * | 9/1992 | Riley | ........... | G01F 23/70 338/176 |
| 5,238,729 A * | 8/1993 | Debe | ........... | G01N 27/127 428/142 |
| 5,855,465 A * | 1/1999 | Boitnott | ........... | H01L 21/67745 414/331.18 |
| 6,175,310 B1 * | 1/2001 | Gott | ........... | G01M 3/165 340/604 |
| 6,550,499 B1 | 4/2003 | Pai | | |
| 6,787,718 B2 * | 9/2004 | Andberg | ........... | G01M 3/165 200/61.04 |
| 8,963,565 B2 * | 2/2015 | Pfeiffer | ........... | G01N 27/126 205/777.5 |
| 2004/0189331 A1 * | 9/2004 | Girshovich | ........... | G01N 27/121 324/694 |
| 2016/0260312 A1 * | 9/2016 | Hazzard | ........... | G08B 21/20 |

OTHER PUBLICATIONS

Official Action dated Jun. 20, 2019, in corresponding Taiwan Patent Application No. 10820568500.

* cited by examiner

*Primary Examiner* — Justin Seo
*Assistant Examiner* — Jean F Morello
(74) *Attorney, Agent, or Firm* — Duane Morris LLP

(57) ABSTRACT

An apparatus includes: a sensor configured to produce a change in a parameter value when in contact with a liquid, wherein the sensor is flexibly linear and configured to traverse a path within a semiconductor processing system; and a controller configured to produce an alert signal based on the change in the parameter value.

20 Claims, 6 Drawing Sheets

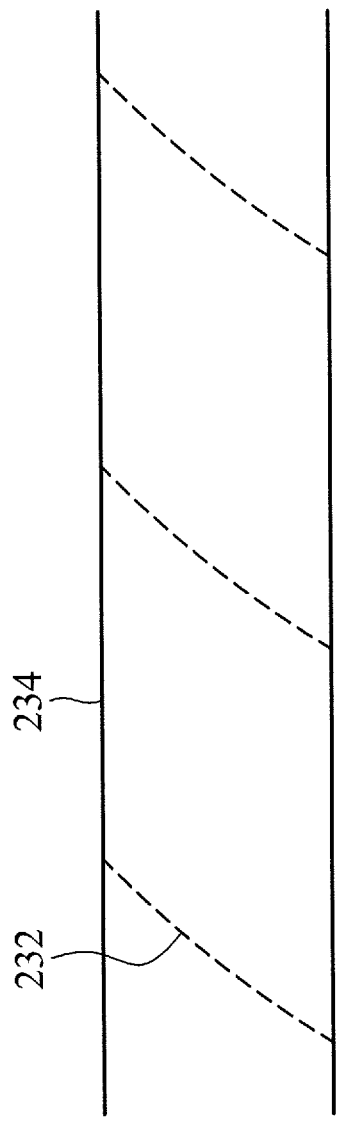

FLEXIBLE LINEAR SENSOR

BACKGROUND

Damaging mediums, such as liquids, may damage a semiconductor device, such as an integrated circuit (IC) and/or semiconductor processing systems (e.g., semiconductor fabrication tools or equipment that process semiconductor devices). This damage may be caused, for example, by corrosion of metal parts of the semiconductor processing system or short-circuiting between electrodes of the semiconductor processing system. Semiconductor processing systems may be exposed to liquids due to a leak in a pipe or other structure that carries liquid, or dew condensation that occurs when a temperature at or inside of a semiconductor processing system goes down to a temperature below a dew point of circumambient air.

The semiconductor industry has made significant advancements in its pursuit of higher device density with lower cost. Technological advances have produced progressively smaller and more complex circuits. In the course of semiconductor device fabrication evolution, functional density (for example, the number of interconnected devices per chip area) has generally increased while geometry sizes have decreased. This scaling down process generally provides benefits by increasing production efficiency and lowering associated costs.

However, increased functional density has increased the complexity of semiconductor devices and semiconductor processing systems, such as by decreasing the size and increasing the sensitivity of semiconductor devices. This increased complexity and sensitivity may be directly related to susceptibility to damage from exposure to damaging mediums, such as damage from a liquid (e.g., liquid damage). Current sensory apparatuses for detecting liquids during semiconductor processing using semiconductor processing systems are restricted to a local area, such as a specific chamber of semiconductor processing system, and do not provide sensory data across larger areas or smaller spaces that may be exposed to liquid. Therefore, conventional systems for semiconductor device processing (e.g., fabrication) are not entirely satisfactory.

BRIEF DESCRIPTION OF THE DRAWINGS

Aspects of the present disclosure are best understood from the following detailed description when read with the accompanying figures. It is noted that various features are not necessarily drawn to scale. In fact, the dimensions and geometries of the various features may be arbitrarily increased or reduced for clarity of discussion.

FIG. 2C is a block diagram that illustrates a flexible linear sensor deployed as a winding around a pipe liquid containment structure, in accordance with some embodiments.

DETAILED DESCRIPTION OF EXEMPLARY EMBODIMENTS

Figure 1:
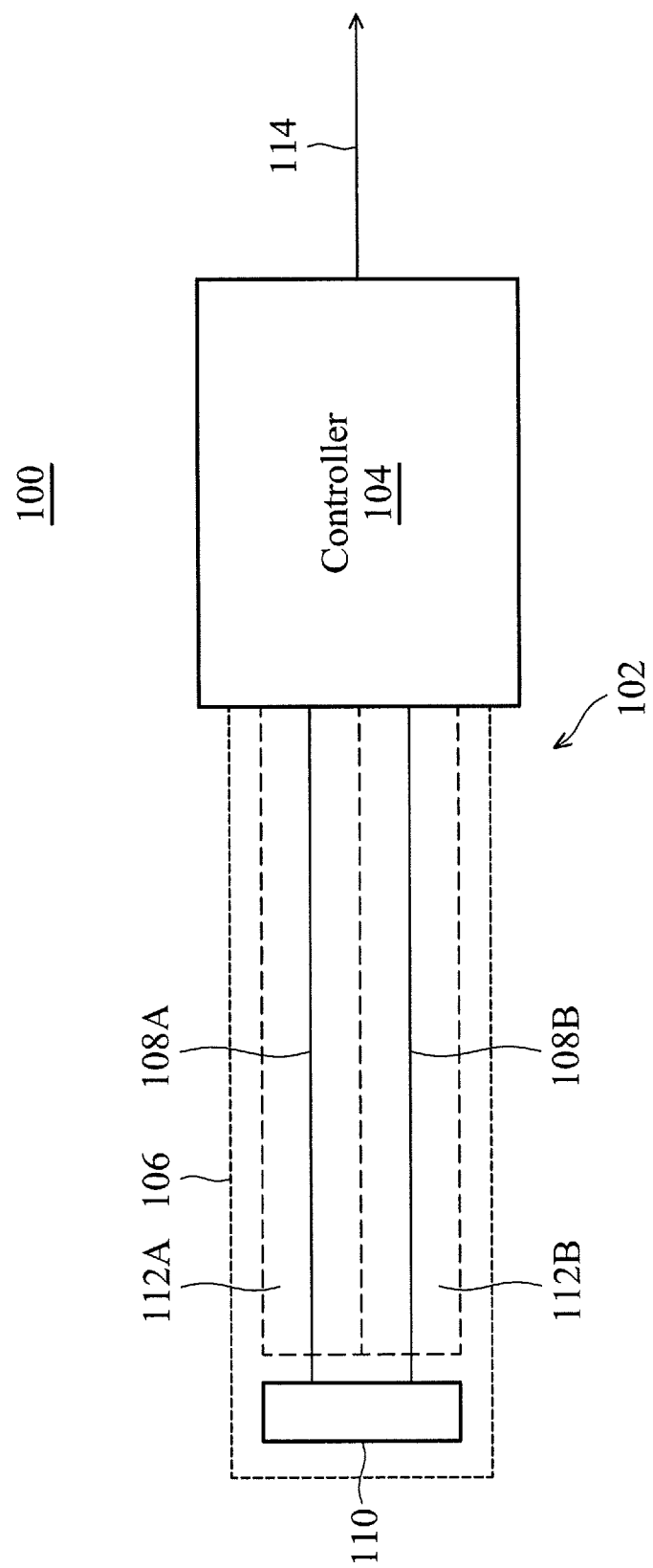
FIG. 1 is a block diagram that illustrates components of a flexible linear sensor, in accordance with some embodiments.

The following disclosure describes various exemplary embodiments for implementing different features of the subject matter. Specific examples of components and arrangements are described below to simplify the present disclosure. These are, of course, merely examples and are not intended to be limiting. For example, it will be understood that when an element is referred to as being "connected to" or "coupled to" another element, it may be directly connected to or coupled to the other element, or one or more intervening elements may be present.

In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure provides various embodiments of a flexible linear sensor. These flexible linear sensors may be utilized during semiconductor processing applications using semiconductor processing systems to detect undesirable exposure of a damaging medium, such as a liquid. This detection may take place within larger, elongated, and/or non-linear (e.g., curved) areas and across through spaces with smaller cross sectional areas that may be more difficult or less cost effective for traditional liquid sensors to cover. Although the discussion below may focus on detection of liquids, any type of damaging medium may be detected that, when contacting the flexible linear sensor, causes a change in a parameter value measurable from a sensor extension.

Flexible linear sensors may include a centralized controller that may interface with at least one sensor extension. These sensor extensions may each include an output wire and an input wire connected by a resistor module. The resistor module may be selected to have a particular resistance so that differences between the voltage, current, impedance, and/or resistance at the output wire or between the input and output wires may be more easily determined (than without a resistor module). For simplicity, resistance and impedance will be discussed interchangeably herein. The output wire and input wire may be covered by an insulation material which may insulate the output wire and input wire for shorting with each other. In certain embodiments, the insulation material may be a fibrous material, such as cotton, which may absorb moisture through capillary action to bring the moisture into contact with the wires for greater sensor extension sensitivity (and ease of exposure) to liquid.

A controller may be configured to perform an alert process for each of the sensor extensions. The alert process may be performed individually for each sensor extension that interfaces with the controller. The alert process may include measuring sensor data (e.g., parameter values) from the sensor extension and determining whether an alert event has occurred based upon the measured sensor data. If an alert event has occurred, the controller may produce an alert signal that indicates the sensor extension at which the alert event has occurred. The alert event may be a change in a measured resistance, voltage, or current difference at or between the input wire and/or the output wire that is indicative of an amount of liquid (e.g., a damaging medium) sensed along the sensor extension. Based on the alert signal, proper remediation measures may be taken, such as cleaning or drying of an area where liquid (e.g., a damaging medium) is detected by the sensor extension.

Flexible linear sensors may comprise a flexibly linear sensing element with a small cross section relative to its length. Accordingly, flexible linear sensors may be able to snake around and sense across semiconductor processing systems. Semiconductor processing systems may be structures (such as chambers or water cooling pipes) that facilitate stages semiconductor processing such as thermal oxidation, thermal flow processing, metal silicidation processing, anneal processing, solidification processing, rapid thermal processing and the like. Also, flexible linear sensors may be more robust, with fewer and simpler components, than traditional liquid sensors. By having fewer and simpler components than traditional liquid sensors, flexible linear sensors may be more cost effective, easily constructed, and with parts more easily replaceable in a modular fashion (e.g., by modularly swapping out parts to be replaced without needing to replace an entire, bespoke semiconductor processing system with integrated liquid sensors). For example, a single controller may have multiple ports to interface modularly with different sensor extensions that are removably attached to the single controller. Accordingly, sensor extensions may be added, replaced, or removed without replacing the controller or other sensor extensions already interfaced with the controller. These multiple sensor extensions may be considered to be connected in parallel with the controller.

FIG. 1 is a block diagram 100 that illustrates components of a flexible linear sensor 102, in accordance with some embodiments. The flexible linear sensor 102 may include a controller 104 that interfaces with at least one sensor extension 106. The sensor extension 106 may include an output wire 108A and an input wire 108B connected via a resistor module 110. The output wire 108A may be insulated with output wire insulation material 112A and the input wire 108B may be insulated with input wire insulation material 112B. In certain embodiments, the output wire insulation material 112A may touch (e.g., abut) the input wire insulation material 112B. The controller 104 may be configured to produce an alert signal 114 in response to detecting an alert event, as will be discussed further below. Although a single sensor extension 106 is illustrated with the controller 104, any number of sensor extensions 106 may be utilized in conjunction with a single controller 104 as desired for different applications in accordance with various embodiments.

The controller may be configured to sense fluctuations in a parameter at the output wire 108B and/or between the input wire 108A and the output wire 108B. For example, the parameter may be voltage, current, resistance, impedance, or any other measurable quantity that may be sensed based on the input wire 108A and the output wire 108B. For simplicity, resistance and impedance will be discussed interchangeably herein. However, in certain embodiments, impedance may refer to a specific internal resistance of a wire (e.g., in relation to length, diameter, and material affected), in contrast with a general discussion of resistance associated with electronic components.

The alert event may be indicative of the input wire 108A or the output wire 108B coming into contact with a damaging medium (e.g., a liquid) in a manner that changes a parameter measurable at the input wire 108A and/or the output wire 108B. This type of contact may be reflective of a short circuit between the input wire 108A and output wire 108B. For example, the controller may detect any non-nominal parameter fluctuation as an alert event. This parameter fluctuation may be an increase and/or a decrease in a parameter such as resistance (in ohms), voltage (in volts), and/or current (in amperes) that exceeds a set threshold value (in ohms, volts, and/or amperes). The term exceed may refer to a change in a value associated with a parameter to become either lower or higher than a threshold value. These non-nominal parameter fluctuations may be indicative of a change in a parameter due to a wire 108 (e.g., either the input wire 108A or output wire 108B) contacting a detrimental substance (e.g., a liquid) that would trigger an alert event. Stated another way, the sensor extension 106 may have a normally open (NO) or normally closed (NC) status and the alert signal may be produced in response to a change in the NO status (e.g., if current or resistance increases) or the NC status (e.g., if current or resistance decrease).

In certain embodiments, the alert signal 114 may be sent to a central processor (not illustrated) for a semiconductor processing system so that an operator of the semiconductor processing system (that the flexible linear sensor is deployed in) may take measures to remediate the liquid detected by the flexible linear sensor. Also, flexible linear sensor 102 may interface with the central processor in a modular fashion such that flexible linear sensors may be added, removed, and/or modified without requiring modification of the central processor.

The resistor module 110 may be connected between the input wire 108A and the output wire 108B. The resistor module 110 may be configured to set a particular resistance value between the input wire 108A and the output wire 108B. In certain embodiments, the input wire 108A and/or the output wire 108B may feature a lower resistance value relative to the resistor module 110. For example, the resistor module 110 may be set to a particular resistance value such as about 10 megaohms (M ohms) to about 20 M ohms such that the variability in resistance values for the sensor extension 106 may be based more upon the resistor module 110 than the resistance at the input wire 108A or the output wire 108B. This may be due at least in part to resistance across the input wire 108A and/or the output wire 108B to be much lower (e.g., an order of magnitude lower) than the resistance value at the resistor module 110. Also, in certain embodiments, setting the resistor module 110 to a resistance value much greater than the resistance across the input wire 108A and/or the output wire 108B may improve (e.g., increase) the sensitivity at which the controller 104 may detect fluctuations in a parameter (e.g., voltage, current, and/or resistance) and the sensor extension 106. In certain embodiments, the resistor module 110 may be separated from (e.g., not touch) the output wire insulation material 112A and/or the input wire insulation material 112B.

The wires 108A and 108B may include a conductive material with low resistance (relative to the resistor module 110). The conductive material may facilitate a current to pass from the input wire 108A to the output wire 108B and for the current to be measurable by the controller 104 at the output wire 108B. Also, the input wire 108A, resistor module 110, and output wires 108B may be linked in series. Therefore, any change at an individual or a combination of the input wire 108A, resistor module 110, and output wires 108B may be manifested as a change in a parameter at the terminus of the input wire 108A and/or output wire 108B and be measurable at the controller 104. Furthermore, the entire sensor extension 106 may be designed to include wires 108A and 108B of different lengths for different applications in different embodiments. In conjunction to being designed with different lengths, the resistance values of the resistor module 110 may also be varied based upon the lengths of the wires 108A and 108B to attain different degrees of sensitivity when parameter values are measured by the controller 104. For example, the resistance value of a resistor module 110 may be set lower when the wires 108A and 108B are longer. Also, various materials of the sensor extension 106 may be linear and flexible, without being restricted to a particular rigid shape. Therefore, the sensor extension 106 may be easily deployed to snake around semiconductor processing systems (e.g., chambers or water cooling pipes) to detect an undesirable presence of a damaging medium (e.g., a liquid) within the semiconductor processing systems.

The output wire 108A may be insulated with output wire insulation material 112A and the input wire 108B may be insulated with input wire insulation material 112B. The insulation material 112A and 112B may be any type of material that may insulate the wires 108A and 108B from short circuiting without the presence of a damaging medium (e.g., a liquid). For example, the insulation material may be a type of dielectric or non-conductive material such as fiberglass, cotton, polyester, and the like. In certain embodiments, the insulation material may be a fibrous insulation material, such as fiberglass, cotton, or polyester, that may draw in liquid that contacts (e.g., touches) the extremities of the insulation material so that the liquid may contact the wires 108A and 108B due to capillary forces between the fibers.

As an exemplary embodiment, the diameter of the input wire 108A and the output wire 108B may be about 0.1 millimeters (mm) to about 0.4 mm. The input wire 108A may be substantially collocated with the output wire 108B with a separation distance effectuated by the respective insulation material between the input wire 108A and the output wire 108B of about 0.01 mm to about 1 mm. The wires 108A, 108B may be about 1 meter (M) long to about 10 M long. The resistor module 110 may be about 10 M ohms to about 20 M ohms. The controller 104 may be calibrated to detect 1 cubic centimeter (cc) of water contacting the wires 108A and 108B as a reduction in resistance across the wires 108A and 108B to less than 1 M ohms. Accordingly, the controller 104 may produce an alert signal from an alert event defined as when the resistance across the wires 108A and 108B falls to less than 1 M ohms.

Figure 2A:
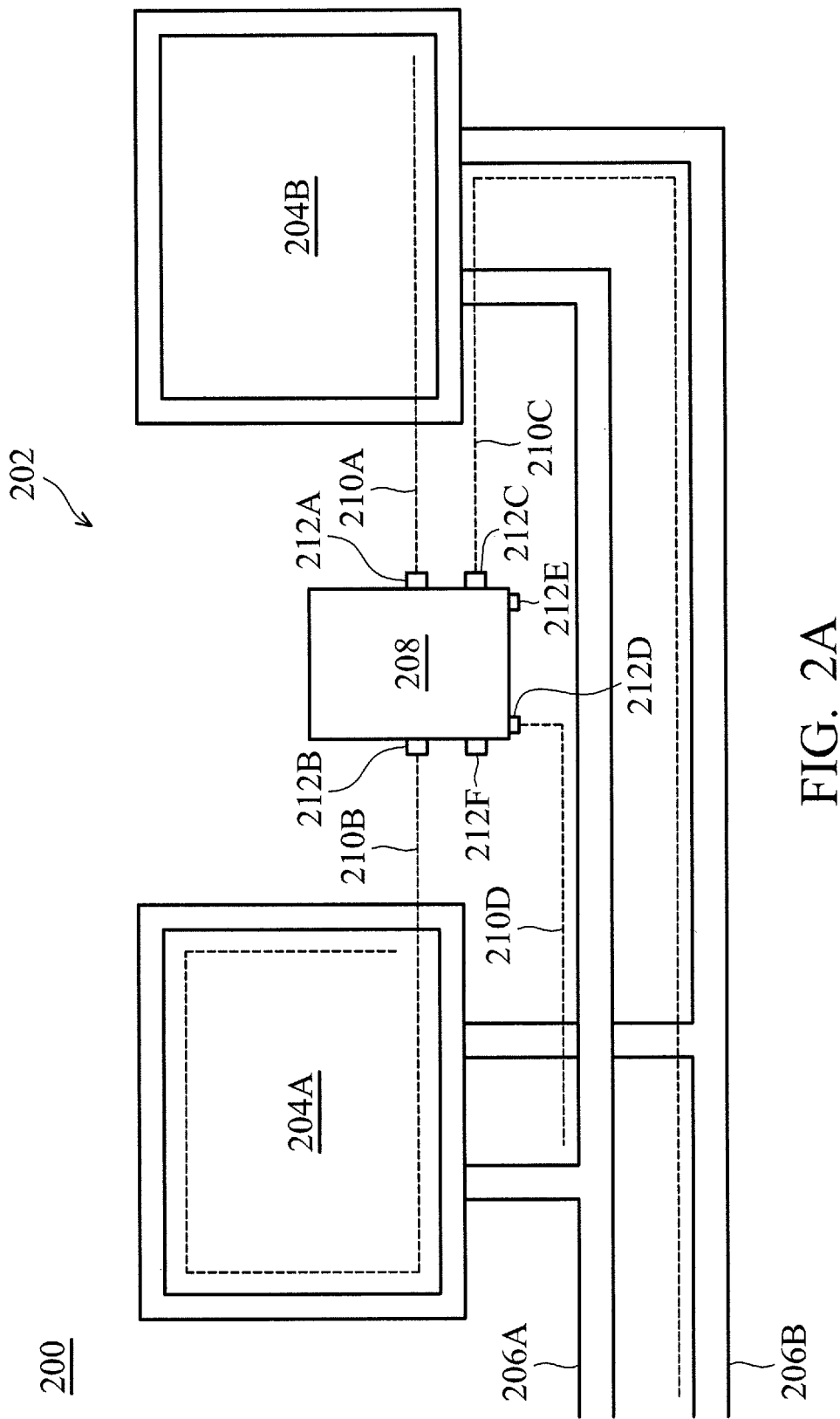
FIG. 2A is a block diagram that illustrates a flexible linear sensor deployed in parallel across different chambers and different liquid containment structures, in accordance with some embodiments.

FIG. 2A is a block diagram 200 that illustrates a flexible linear sensor 202 deployed in parallel across different chambers 204A-204B and different liquid containment structures 206A-206B (e.g., pipes), in accordance with some embodiments. The flexible linear sensor 202 may include a single controller 208 with multiple sensor extensions 210A-210D. Each of the multiple sensor extensions 210A-210D are indicated with dotted lines and, for simplicity, omit certain details of sensor extensions already discussed above in connection with FIG. 1.

The chambers 204A and 204B as well as the liquid containment structures 206A and 206B may be part of a semiconductor processing system. The liquid containment structure 206A may be a liquid cooling intake pipe for each of chambers 204A and 204B (e.g., providing cooling liquid into each of chambers 204A and 204B). Also, liquid containment structure 206B may be a liquid cooling outtake pipe for each of chambers 204A and 204B (e.g., removing warmed cooling liquid from each of chambers 204A and 204B). The chambers 204A and 204B may be locations for different treatments during semiconductor processing, such as thermal oxidation, thermal flow processing, metal silicidation processing, anneal processing, solidification processing and the like.

The controller 208 may include ports 212A-212F via which the sensor extensions 210A-210D may interface with the controller. Accordingly, a single controller 208 may have multiple ports 212A-212F to interface modularly with different sensor extensions 210A-210D. For example, ports 212A-212D may be interfaced with sensor extensions 210A-210D. However, open ports 212E and 212F may not currently be interfaced with any sensor extensions but may in the future interface with a sensor extension that is currently plugged into the open ports 212E and 212F. Also, sensor extensions plugged into different ports may be moved (e.g., swapped), such as where sensor extension 210C may be swapped with sensor extension 212D or may be alternatively plugged into port 212E instead of being plugged into port 212C. Accordingly, sensor extensions 210A-210D may be added, replaced, or removed without replacing the controller 208 or other sensor extensions 210A-210D already interfaced with the controller 208.

The multiple sensor extensions 210A-210D may be considered to be connected in parallel with the controller 208. By being connected in parallel, the controller 208 may be configured to perform an alert process for each of the sensor extensions 210A-201D individually. For example, the controller 208 may be configured to perform an alert process for sensor extension 210A to determine whether a non-nominal fluctuation in a parameter is detected within the chamber 204B. Also, the controller 208 may be configured to perform another alert process for sensor extension 210B to determine whether a non-nominal fluctuation in a parameter is detected within the chamber 204A. Also, the controller 208 may be configured to perform another alert process for sensor extension 210C to determine whether a non-nominal fluctuation in a parameter is detected within the vicinity of liquid containment structure 206B. Also, the controller 208 may be configured to perform another alert process for sensor extension 210D to determine whether a non-nominal fluctuation in a parameter is detected within the vicinity of liquid containment structure 206A. As discussed above, the non-nominal fluctuations in a parameter may be indicative of liquid (e.g., a damaging medium) being detected by any one of the sensor extensions 210A-210D.

Also, the sensor extensions 210A-210D may be of any length or geometry as desired for different applications in accordance with different embodiments. For example, sensor extension 210C may be longer than sensor extension 210B. Also, sensor extension 210D may be of similar, but not the same, length as sensor extension 210A. Furthermore, sensor extensions 210A-210D may cover different parts of the semiconductor processing system to different degrees. For example, sensor extension 210B may cover a substantially larger portion of chamber 204A than sensor extension 210A covers for chamber 204B. Also, sensor extension 210C may cover (e.g., traverse a path along) a substantially larger portion of liquid containment structure 206B than sensor extension 210D covers for liquid containment structure 206A.

Figure 2B:
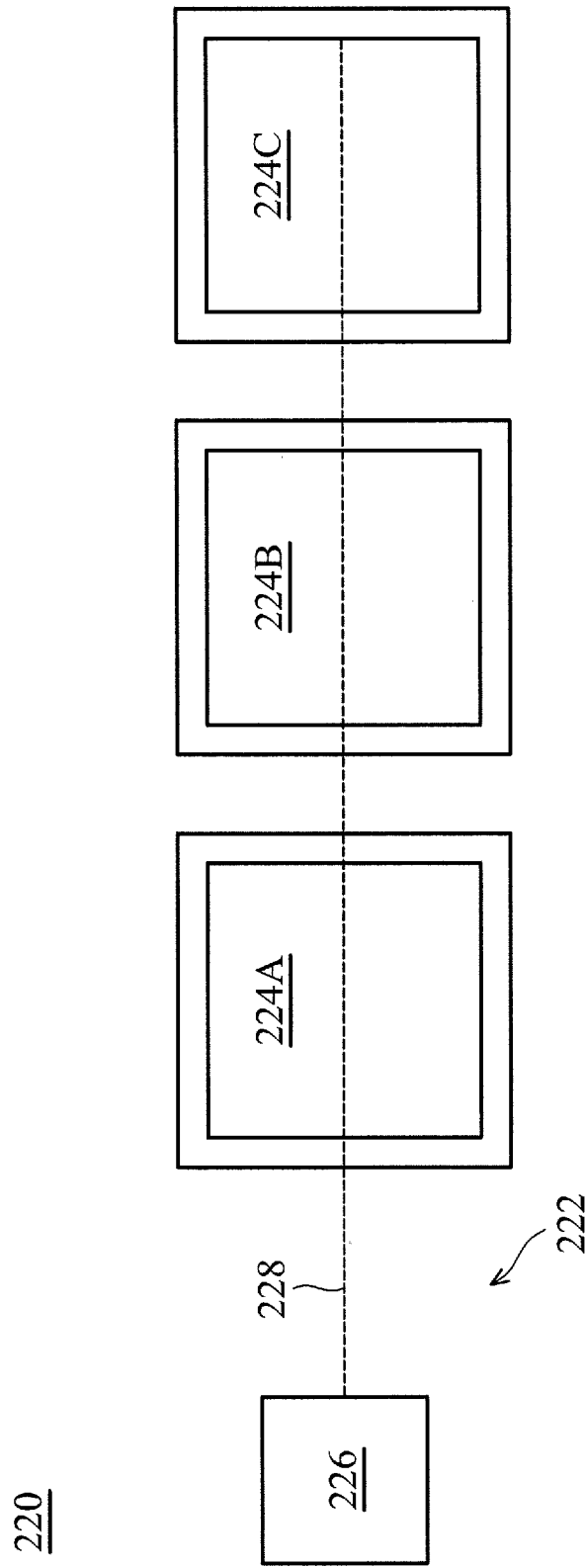
FIG. 2B is a block diagram that illustrates a flexible linear sensor deployed across multiple chambers in series, in accordance with some embodiments.

FIG. 2B is a block diagram 220 that illustrates a flexible linear sensor 222 deployed across multiple chambers 224A-224C in series, in accordance with some embodiments. The flexible linear sensor 222 may include a controller 226 and a sensor extension 228. The sensor extension 228 is indicated with dotted lines and, for simplicity, omits certain details of sensor extensions already discussed above in connection with FIG. 1. The chambers 224A-224C may be locations for different treatments during semiconductor processing, such as thermal oxidation, thermal flow processing, metal silicidation processing, anneal processing, solidification processing and the like. An alert process may be performed by the controller 226 based on the sensor extension 228 across the multiple chambers 224A-224C in series. For example, the controller 226 may perform an alert process for sensor extension 228 to determine whether a non-nominal fluctuation in a parameter is detected within any of chambers 224A-224C. As discussed above, the non-nominal fluctuations in a parameter may be indicative of a damaging medium (e.g., a liquid) being detected by the sensor extension 228 in any of the chambers 224A-224C.

FIG. 2C is a block diagram that illustrates a sensor extension 232 of a flexible linear sensor deployed as a winding around a pipe liquid containment structure 234, in accordance with some embodiments. The sensor extension 232 may be connected to a controller of the flexible linear sensor, as discussed further in connection with FIG. 1. By being wound around the pipe liquid containment structure 234, the sensor extension 232 may wrap around and be collocated with the pipe liquid containment structure 234 and able to detect whether liquid is present on the outside of the pipe liquid containment structure 234.

Although FIG. 2C illustrates the flexible linear sensor 222 deployed as a winding around the pipe liquid containment structure 234, the flexible linear sensor 222 may be deployed in other manners as desired for collocation with a liquid containment structure in accordance with various embodiments. For example, the flexible linear sensor 222 may be deployed as a winding around a liquid containment structure that is a reservoir, such as by being along an upper edge of a reservoir just about the water line.

Figure 2D:
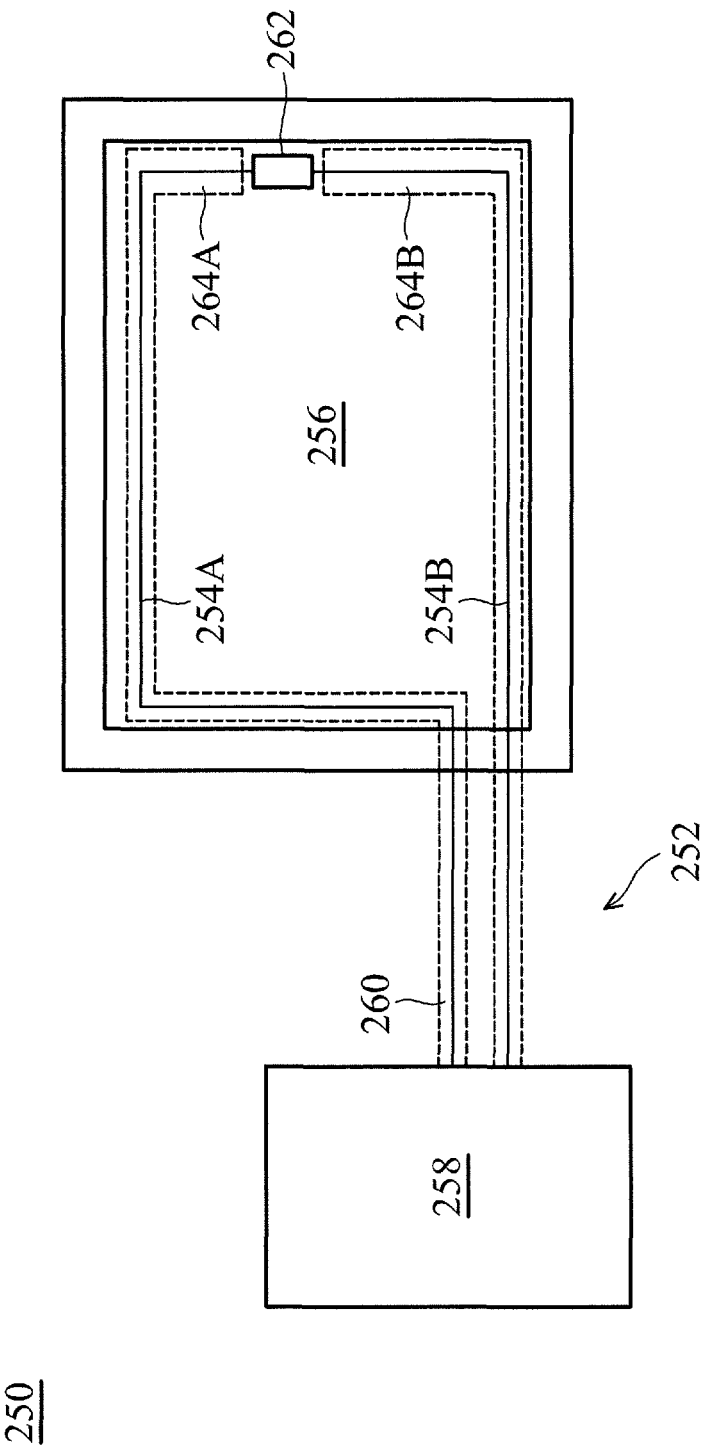
FIG. 2D is a block diagram that illustrates a flexible linear sensor with wires that are separated and not collocated, in accordance with some embodiments.

FIG. 2D is a block diagram 250 that illustrates a flexible linear sensor 252 with input and output wires 254A and 254B that are separated and not collocated while within a chamber 256, in accordance with some embodiments. The flexible linear sensor 252 may include a controller 258 that interfaces with a sensor extension 260. The sensor extension 260 may include the input wire 254A and the output wire 254B connected with a resistor module 262. The input wire 254A may be insulated with input wire insulation material 264A. The output wire 254B may be insulated with output wire insulation material 264B. The controller 258 may be configured to perform an alert process for sensor extension 228 to determine an alert event as a non-nominal fluctuation in a parameter is detected within the chamber 256. As discussed above, the non-nominal fluctuations in a parameter may be indicative of liquid being detected by the sensor extension 260 in the chamber 256. Also, while within the chamber 256, the input wire 254A may be separated from and not be collocated with the output wire 254B. By separating the input wire 254A from the output wire 254B, the sensor extension 228 may cover (e.g., be configured for collection of sensor data or parameter values over) a portion of the chamber 256 using less quantity of the input wire 254A and output wire 254B than if the input wire 254A and output wire 254B were collocated and both had to traverse the same parts of the chamber 256.

Figure 3:
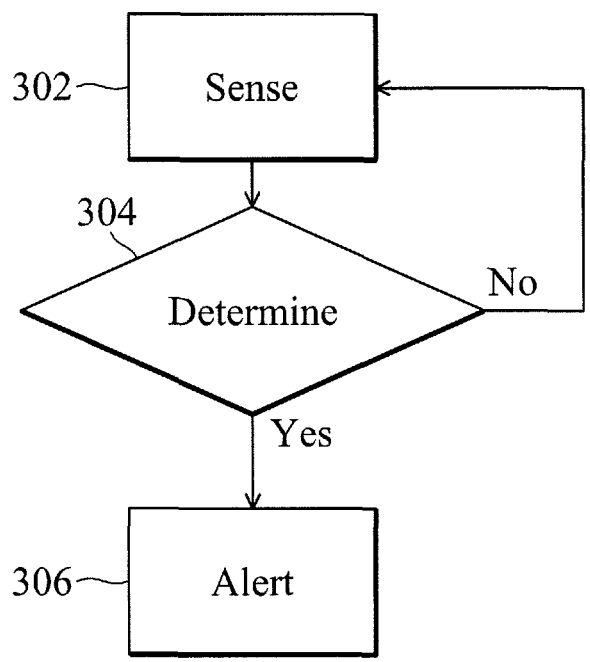
FIG. 3 is a flow chart of an alert process, in accordance with some embodiments.

FIG. 3 is a flow chart of an alert process 300, in accordance with some embodiments. At step 302, a controller may read a parameter value (e.g., voltage, current, or resistance value) from an output wire and/or input wire of a flexible linear sensor. At step 304, the controller may determine whether the parameter value is a non-nominal fluctuation. If the parameter value is not indicative of a non-nominal fluctuation, the alert process may return to step 302. If the parameter value is indicative of a non-nominal fluctuation, the alert process may proceed to step 306. At step 306, the controller may classify the non-nominal fluctuation as an alert event and produce an alert signal. As discussed above, the non-nominal fluctuation may be a change in a measured parameter (e.g., resistance, voltage, or current) that is indicative of an amount of liquid (e.g., a damaging medium) sensed along the sensor extension. Optionally, the alert signal may be sent to a central processor, as discussed above. Based on the alert signal, proper remediation measures may be taken, such as cleaning or drying of an area where liquid (e.g., a damaging medium) is detected by the sensor extension.

In an embodiment, an apparatus includes: a sensor configured to produce a change in a parameter value when in contact with a liquid, wherein the sensor is flexibly linear and configured to traverse a path within a semiconductor processing system; and a controller configured to produce an alert signal based on the change in the parameter value.

In another embodiment, a method includes: reading a parameter value at a sensor configured to produce a change in the parameter value when in contact with a liquid, wherein the sensor is flexibly linear and configured to traverse a path within a semiconductor processing system; determining whether the parameter value exceeds a threshold; and producing an alert signal in response to determining that the parameter value exceeds the threshold.

Yet in another embodiment, an apparatus includes: a plurality of sensors configured to produce a change in a parameter value when in contact with a liquid, wherein each of the plurality of sensors is flexibly linear and configured to traverse different respective paths within a semiconductor processing system; and a controller interfaced with each of the plurality of sensors and configured to produce an alert signal based on the change in the parameter value.

The foregoing outlines features of several embodiments so that those ordinary skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Additionally, persons of skill in the art would be enabled to configure functional entities to perform the operations described herein after reading the present disclosure. The term "configured" as used herein with respect to a specified operation or function refers to a system, device, component, circuit, structure, machine, etc. that is physically or virtually constructed, programmed and/or arranged to perform the specified operation or function.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. An apparatus, comprising:
    a sensor comprising a closed circuit, wherein the sensor is configured to produce a change in a closed circuit parameter value of the closed circuit when in contact with a liquid, wherein the sensor is flexibly linear and configured to traverse a path within a semiconductor processing system; and
    a controller configured to produce an alert signal based on the change in the closed circuit parameter value.

2. The apparatus of claim 1, wherein the sensor comprises an input wire and an output wire, the input wire and the output wire connected by a resistor module and coupled to the controller.

3. The apparatus of claim 2, wherein the resistor module comprises a resistance value that is greater than a resistance value across part of the input wire or across part of the output wire.

4. The apparatus of claim 2, wherein the input wire and the output wire are at least partially enveloped in a fibrous insulation material configured to draw liquid that touches the fibrous insulation material toward at least one of the input wire and the output wire via capillary forces.

5. The apparatus of claim 2, wherein the input wire and the output wire are collocated and traverse a same part of the semiconductor processing system.

6. The apparatus of claim 2, wherein the input wire and the output wire are separated and traverse different parts of the semiconductor processing system.

7. The apparatus of claim 1, further comprising a plurality of sensors coupled to the controller, each of the plurality of sensors being flexibly linear and configured to traverse different respective paths within the semiconductor processing system.

8. The apparatus of claim 1, wherein the controller comprises an open port and wherein the sensor is removably attached to the controller such that the sensor is configured to be removed from the controller and reattached to the controller at the open port.

9. The apparatus of claim 1, wherein the controller is configured to produce the alert signal when the closed circuit parameter value exceeds a threshold.

10. A method, comprising:
    reading a closed circuit parameter value at a sensor comprising a closed circuit, wherein the sensor is configured to produce a change in the closed circuit parameter value of the closed circuit when in contact with a liquid, wherein the sensor is flexibly linear and configured to traverse a path within a semiconductor processing system;
    determining whether the closed circuit parameter value exceeds a threshold; and
    producing an alert signal in response to determining that the closed circuit parameter value exceeds the threshold.

11. The method of claim 10, wherein the closed circuit parameter value is read from at least one of an input wire and an output wire of the sensor.

12. The method of claim 10, wherein the path is within a chamber of the semiconductor processing system.

13. The method of claim 10, wherein the path wraps around a water pipe of the semiconductor processing system.

14. The method of claim 10, wherein the path traverses several chambers of the semiconductor processing system.

15. An apparatus, comprising:
    a plurality of sensors each comprising a respective closed circuit, wherein each of the plurality of sensors is configured to produce a change in a closed circuit parameter value of the respective closed circuit when in contact with a liquid, wherein each of the plurality of sensors is flexibly linear and configured to traverse different respective paths within a semiconductor processing system; and
    a controller interfaced with each of the plurality of sensors and configured to produce an alert signal based on the change in the closed circuit parameter value.

16. The apparatus of claim 15, wherein each of the plurality of sensors comprise an input wire, an output wire, and a resistor module, wherein the input wire and the output wire are connected by the resistor module and coupled to the controller.

17. The apparatus of claim 16, wherein the input wire and the output wire are at least partially enveloped in a fibrous insulation material configured to draw in liquid that touches the fibrous insulation material via capillary forces.

18. The apparatus of claim 15, wherein at least one of the plurality of sensors comprise an input wire and an output wire that are collocated and traverse a same part of the semiconductor processing system.

19. The apparatus of claim 18, wherein at least one sensor of the plurality of sensors traverses two chambers of the semiconductor processing system.

20. The apparatus of claim 15, wherein each of the plurality of sensors traverses different chambers of the semiconductor processing system.

* * * * *